United States Patent
Kendrick et al.

(10) Patent No.: US 10,987,252 B2
(45) Date of Patent: *Apr. 27, 2021

(54) SYSTEMS, METHODS, AND DEVICES FOR TREATING A TISSUE SITE ON A MAMMAL HAVING HAIR PROXIMATE THE TISSUE SITE

(71) Applicant: KCI Licensing, Inc., San Antonio, TX (US)

(72) Inventors: Rosella Kendrick, Stourbridge (GB); Colin John Hall, Poole (GB); Elliott James Rider, Middlesbrough (GB); Timothy Mark Robinson, Shillingstone (GB); Benjamin Stokes, Ringwood (GB)

(73) Assignee: KCI Licensing, Inc., San Antonio, TX (US)

( * ) Notice: Subject to any disclaimer, the term of this patent is extended or adjusted under 35 U.S.C. 154(b) by 324 days.

This patent is subject to a terminal disclaimer.

(21) Appl. No.: 15/996,820

(22) Filed: Jun. 4, 2018

(65) Prior Publication Data
US 2018/0280203 A1 Oct. 4, 2018

Related U.S. Application Data

(63) Continuation of application No. 13/937,947, filed on Jul. 9, 2013, now Pat. No. 10,010,454.
(Continued)

(51) Int. Cl.
*A61L 15/18* (2006.01)
*A61L 15/26* (2006.01)
(Continued)

(52) U.S. Cl.
CPC ...... *A61F 13/0246* (2013.01); *A61F 13/0206* (2013.01); *A61F 13/0209* (2013.01);
(Continued)

(58) Field of Classification Search
CPC .............. A61F 13/0246; A61F 13/0206; A61F 13/0209; A61F 13/0213; A61F 13/0216;
(Continued)

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Andrew J Mensh

(57) ABSTRACT

Systems, methods, and devices are presented for treating a tissue site and managing hair proximate the tissue site. A composition is provided for inhibiting, removing, or weakening hair proximate the tissue site and for providing an improved fluid seal by a flexible film drape over the tissue site. In some example embodiments, a hair-modification agent is disposed at least proximate a peripheral edge of a treatment manifold between a drape and epidermis proximate a tissue site. The hair-modification agent can be configured to flow over imperfections on the epidermis and to form a fluid seal against the epidermis, and can further be configured to at least substantially weaken hair on the epidermis as the hair encounters the hair-modification agent.

33 Claims, 5 Drawing Sheets

Related U.S. Application Data

(60) Provisional application No. 61/669,395, filed on Jul. 9, 2012.

(51) Int. Cl.
*A61F 13/02* (2006.01)
*A61L 15/44* (2006.01)
*A61L 15/46* (2006.01)

(52) U.S. Cl.
CPC ...... *A61F 13/0213* (2013.01); *A61F 13/0216* (2013.01); *A61L 15/18* (2013.01); *A61L 15/26* (2013.01); *A61L 15/44* (2013.01); *A61L 15/46* (2013.01); *A61F 13/02* (2013.01); *A61L 2300/434* (2013.01)

(58) Field of Classification Search
CPC .......... A61L 15/18; A61L 15/26; A61L 15/44; A61L 15/46; A61L 2300/434
USPC ....................................................... 604/319
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A * | 5/1983 | Svedman ........... | A61F 13/00068 604/114 |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,842,610 A * | 6/1989 | Gordon ................... | A61K 8/97 8/160 |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,021,319 A * | 6/1991 | Kakimi ................... | G03F 7/002 430/138 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0028392 A1 * | 2/2010 | Cawthorne ............ | A61K 8/46 424/401 |
| 2010/0069858 A1 * | 3/2010 | Olson .................... | A61F 13/0216 604/319 |

(56) References Cited

U.S. PATENT DOCUMENTS

| | | | | |
|---|---|---|---|---|
| 2010/0272784 | A1* | 10/2010 | Kantner | C09J 139/06 |
| | | | | 424/448 |
| 2010/0310671 | A1* | 12/2010 | Malotky | C08F 8/44 |
| | | | | 424/501 |
| 2014/0163491 | A1 | 6/2014 | Schuessler et al. | |
| 2015/0080788 | A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 1129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 16-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, ŽMaksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of its

(56) References Cited

OTHER PUBLICATIONS

Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

SYSTEMS, METHODS, AND DEVICES FOR TREATING A TISSUE SITE ON A MAMMAL HAVING HAIR PROXIMATE THE TISSUE SITE

RELATED APPLICATION

The present invention in a continuation of U.S. patent application Ser. No. 13/937,947, entitled "SYSTEMS, METHODS, AND DEVICES FOR TREATING A TISSUE SITE ON A MAMMAL HAVING HAIR PROXIMATE THE TISSUE SITE," filed Jul. 9, 2013 which claims the benefit, under 35 USC § 119(e), of the filing of U.S. Provisional Patent Application Ser. No. 61/669,395, entitled "SYSTEMS, METHODS, AND DEVICES FOR TREATING A TISSUE SITE ON A MAMMAL HAVING HAIR PROXIMATE THE TISSUE SITE," filed 9 Jul. 2012, which is incorporated herein by reference for all purposes.

TECHNICAL FIELD

The present invention relates generally to tissue treatment systems and more particularly, but without limitation, to a dressing having a hair-modification agent to modify hair adjacent a tissue site.

BACKGROUND

Dressings are often used to treat a tissue site of a patient. A dressing may include many elements that are selected to generally promote growth or healing of tissue. Typically, a dressing may be placed next to a tissue site, such as an open wound, for example. The dressing may cover the tissue site to prevent the tissue site from becoming undesirably dry, prevent contamination of the tissue site from foreign agents, such as undesirable bacteria, and prevent further injury to the tissue site. To accomplish these tasks, dressings are often secured to tissue adjacent the tissue site with an adhesive.

Using adhesives to secure a dressing can keep the dressing in place over a tissue site and limit inadvertent removal of the dressing that may lead to contamination or re-injury of the tissue site. Unfortunately, the adhesive may also irritate the tissue adjacent the tissue site and can cause pain to a patient when the dressing is removed. The pain may be associated in part with removal of hair bonded to the adhesive.

Some dressings may be applied to the tissue site for extended periods. For example, a dressing used with reduced-pressure therapy can be left in place for many days. Hair growth under the dressing during such therapy may cause leaks, as well as increased pain upon removal of the dressing.

SUMMARY

According to an illustrative, non-limiting embodiment, a dressing for treating a tissue site is described. The dressing includes a gasket having a sealing agent and a hair-modification agent associated with the sealing agent. The hair-modification agent is configured to modify hair on epidermis proximate the tissue site.

According to another illustrative, non-limiting embodiment, a system for treating a tissue site is described. The system includes a pad having a peripheral edge and a drape adapted to cover the pad to form a sealed space containing the pad. The system also includes a hair-modification agent adapted to be disposed proximate the peripheral edge of the pad. The hair-modification agent may be further adapted to be disposed adjacent at least a portion of an epidermis to modify hair on the epidermis proximate the tissue site.

According to another illustrative, non-limiting embodiment, a dressing for treating a tissue site is described. The dressing includes a treatment pad having a peripheral edge and a drape adapted to cover the treatment pad to form a sealed space containing the treatment pad. The dressing may also include a hair-modification layer having a hair-modification agent disposed therein. The hair-modification layer may be adapted to be disposed at least proximate the peripheral edge of the treatment pad and to be disposed adjacent at least a portion of an epidermis proximate the tissue site to seal the drape to and modify hair on the epidermis.

According to another illustrative, non-limiting embodiment, a method for treating a tissue site is described. The method disposes a manifold having a peripheral edge adjacent the tissue site and disposes a gasket having a sealing agent and a hair-modification agent proximate the peripheral edge of the manifold and adjacent at least a portion of an epidermis. The method disposes a drape over the manifold and the gasket to form a sealed space containing the manifold.

Other objects and advantages of the illustrative embodiments will become apparent with reference to the drawings and detailed description that follow.

DETAILED DESCRIPTION OF ILLUSTRATIVE EMBODIMENTS

Figure 1:
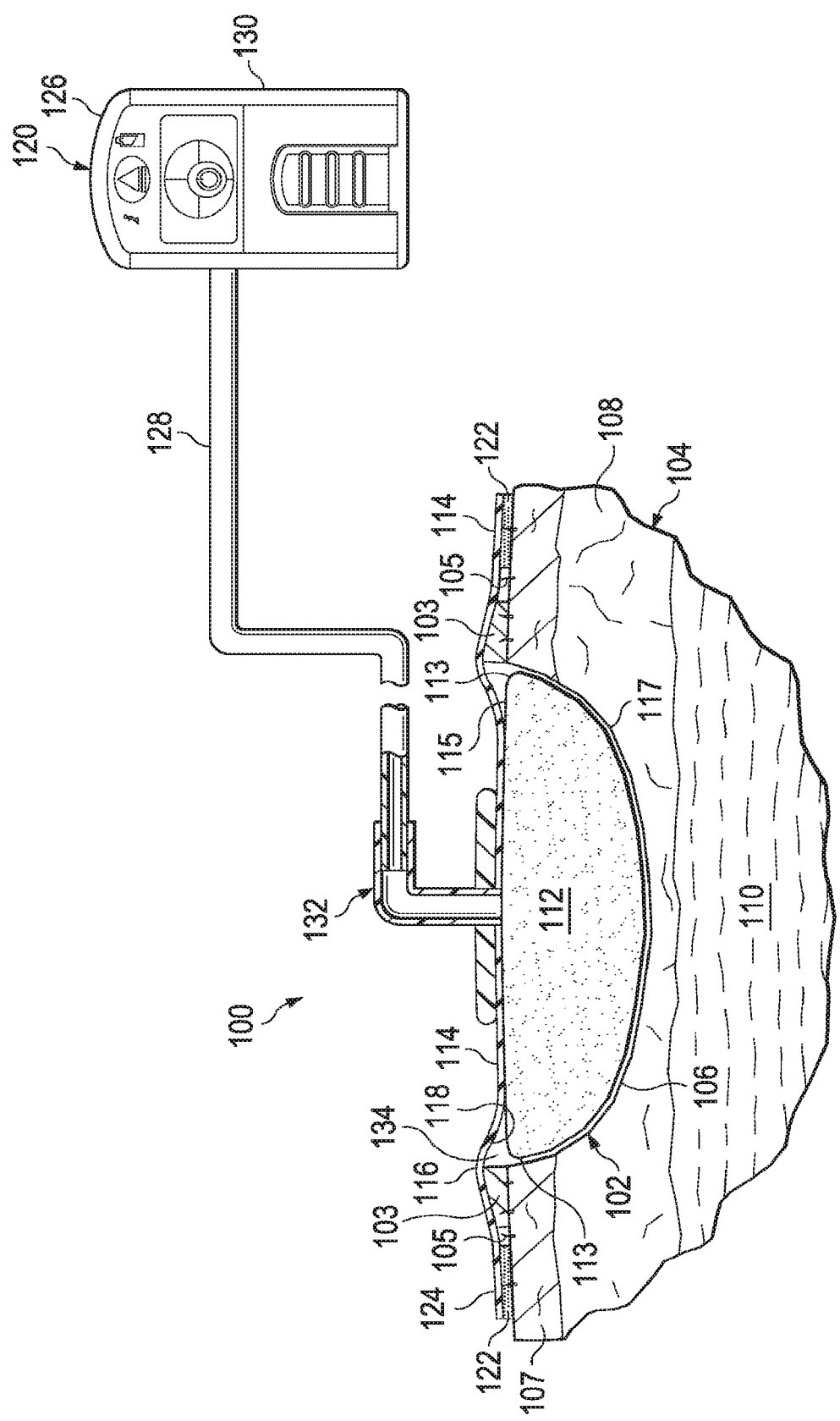
FIG. 1 is a schematic diagram with a portion shown in cross section of an illustrative embodiment of a system for treating a tissue site, which has hair proximate the tissue site.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

In treating a tissue site on a patient, a dressing may often be used to secure the dressing to the tissue site. The dressing may be secured with an adhesive that bonds to the dressing and to tissue that may be adjacent the tissue site. In some cases, the adhesive may irritate the tissue adjacent the tissue site. In some cases, the adhesive may bond to hair on the tissue adjacent the tissue site. When the dressing is removed, such as when the tissue site is healed or a new dressing is required, for example, the adhesive may pull hair out of the tissue adjacent the tissue site, causing the patient pain.

Dressings are commonly applied to tissues sites in conjunction with reduced-pressure therapy, which can augment and accelerate growth of new tissue. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure therapy," but is also known by other names, including "negative-pressure wound therapy," "negative-pressure therapy," "vacuum therapy," and "vacuum-assisted closure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

In treating a tissue site on a patient (human or other animal) with reduced pressure, an adequate fluid seal is required. With at least some dressings using relatively low-flow reduced-pressure sources or in situations in which the dressing remains in place for an extended duration, hair, fur, or hair-like coverings may cause an unacceptable leak rate or otherwise interfere with the therapeutic application of reduced-pressure. Moreover, when removing a dressing after an extended period, considerable pain may be caused to the patient if hair has become adhered to the dressing.

As disclosed herein, systems, methods, and devices for treating a tissue site can overcome these shortcomings and others. Exemplary embodiments described herein can substantially reduce or eliminate irritation and pain that may be associated with using or removing dressings. Exemplary embodiments are also described that can substantially reduce or eliminate leaks caused by hair growth proximate the tissue site. In some embodiments, a hair management system is described that can inhibit, remove, weaken, or otherwise modify hair. In yet more particular embodiments, a hair-modification agent is disposed or adapted to be disposed adjacent an epidermis to modify hair on the epidermis proximate a tissue site.

Figure 2:
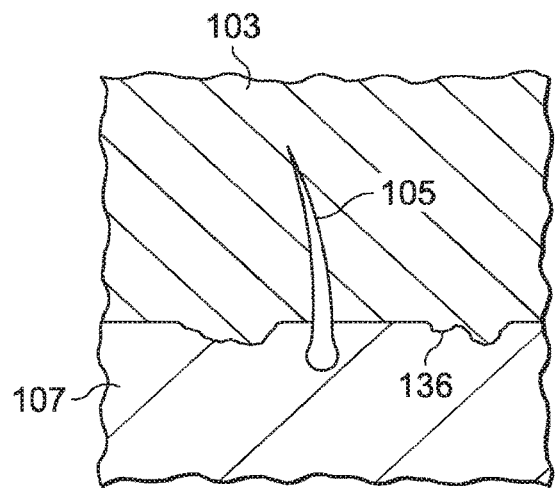
FIG. 2 is a cross sectional view of an illustrative embodiment of a composition for sealing and modifying hair on an epidermis.
Figure 3:
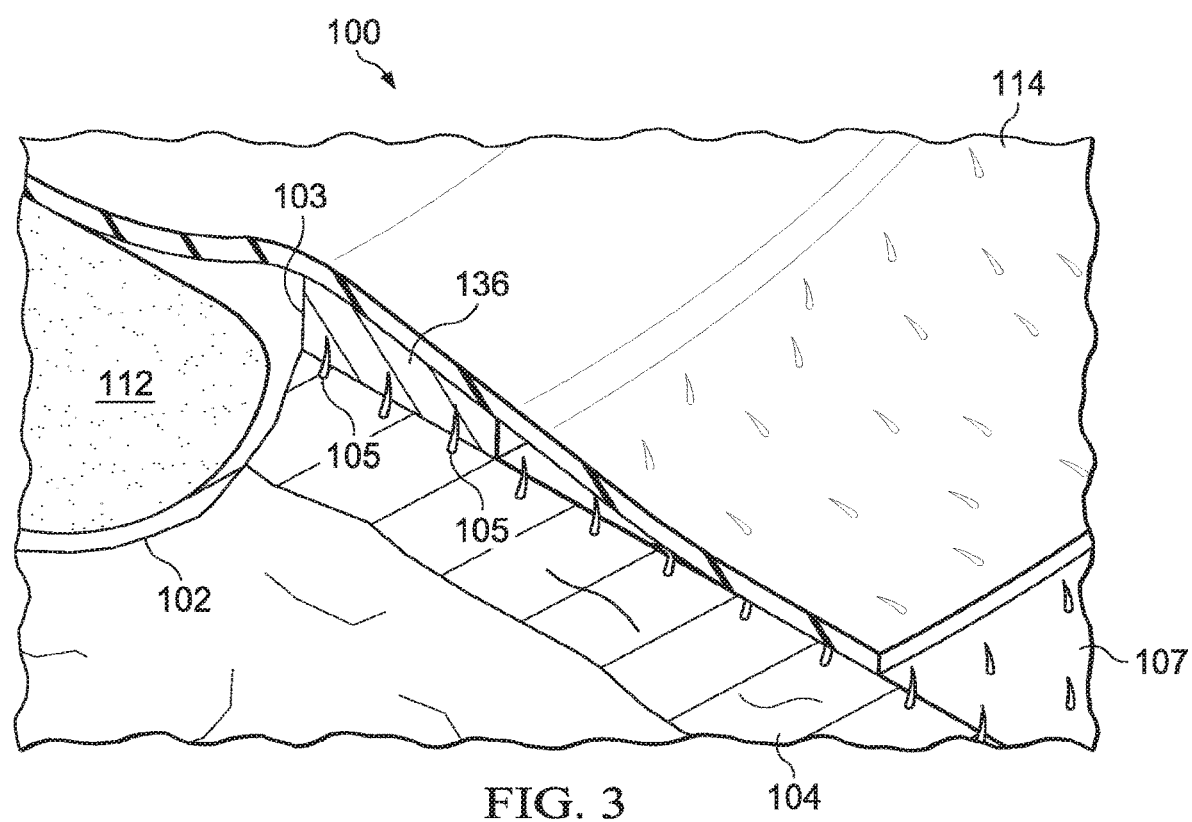
FIG. 3 is a perspective cross-sectional view of a portion of a system for treating a tissue site, which has hair proximate the tissue site.

Referring now to the drawings and, more specifically to FIG. 1, an illustrative embodiment of a system 100 for applying reduced pressure to a tissue site 102 on a patient 104 is presented, where the patient 104 has hair 105 proximate the tissue site 102, as shown in more detail in FIGS. 2 and 3. The system 100 may include a composition 103, which may be formed as a ring, a gasket, or other flexible annular member. In some embodiments, the composition 103 may form a fluid seal. In some embodiments, the composition 103 may manage hair proximate the tissue site 102. In some embodiments, the composition 103 may form a fluid seal and manage hair proximate the tissue site 102. The tissue site 102 may be, for example, a wound 106. The wound 106 may include, without limitation, any irregularity with a tissue, such as an open wound, surgical incision, or diseased tissue. The wound 106 is shown extending through an epidermis 107, or generally skin, and a dermis 108 and reaching into a hypodermis, or a subcutaneous tissue 110. The system 100 may be used to treat a tissue site, such as a wound of any depth, as well as many different types of tissue sites including open wounds or intact tissue. The tissue site 102 may be the bodily tissue of an organism, including bone tissue, adipose tissue, muscle tissue, dermal tissue, vascular tissue, connective tissue, cartilage, tendons, ligaments, or other tissue.

The system 100 generally includes a treatment pad such as a treatment manifold 112, a drape such as a flexible film drape 114, and a reduced-pressure source such as a reduced-pressure subsystem 120. The treatment manifold 112 may be operable to distribute reduced pressure. The flexible film drape 114 may provide a fluid seal over the treatment manifold 112 and the tissue site 102. "Fluid seal," or "seal," may include a seal adequate to maintain reduced pressure at a desired site given the particular reduced-pressure source or subsystem involved. The system 100 may include an attachment device 122 to help form a fluid seal between the flexible film drape 114 and the epidermis 107. The flexible film drape 114 has a first side 116 and a second side 118.

The treatment manifold 112 may be positioned between the second side 118 of the flexible film drape 114 and the tissue site 102. The treatment manifold 112 may have a peripheral edge 113 that is the most outboard portion of the treatment manifold 112. The treatment manifold 112 may have a first side 115 and a second side 117.

The term "manifold" as used herein generally refers to a substance or structure that is provided to assist in applying reduced pressure to, delivering fluids to, or removing fluids from a tissue site, e.g., the tissue site 102. The treatment manifold 112 includes a plurality of flow channels or pathways that distribute fluids provided to and removed from the tissue site 102 around the treatment manifold 112. In one illustrative embodiment, the flow channels or pathways are interconnected to improve distribution of fluids provided to or removed from the tissue site 102. The treatment manifold 112 may include one or more of the following: a biocompatible material that is capable of being placed in contact with the tissue site 102 and distributing reduced pressure to the tissue site 102. The treatment manifold 112 may also include devices that have structural elements arranged to form flow channels, such as, for example, cellular foam, open-cell foam, porous tissue collections, liquids, gels, and foams that include, or cure to include, flow channels. The treatment manifold 112 may further include porous material, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material. The treatment manifold 112 may still further include a scaffold material. In some situations, the treatment manifold 112 may also be used to distribute fluids such as medications, antibacterials, growth factors, and various solutions to the tissue site 102. Other layers may be included in or on the treatment manifold 112, such as absorptive materials, wicking materials, hydrophobic materials, and hydrophilic materials.

In one illustrative, non-limiting embodiment, the treatment manifold 112 may be constructed from a bioresorbable material that may remain in a patient's body following use of the reduced-pressure dressing. Suitable bioresorbable materials may include, without limitation, a polymeric blend of polylactic acid (PLA) and polyglycolic acid (PGA). The polymeric blend may also include without limitation polycarbonates, polyfumarates, and capralactones. The treatment manifold 112 may further serve as a scaffold for new cell-growth, or a scaffold material may be used in conjunction with the treatment manifold 112 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The flexible film drape 114 may be sized so that the flexible film drape 114 overlaps the wound 106 in such a manner that a portion of the flexible film drape 114 extends beyond the periphery of the wound 106 to form an extension 124. The flexible film drape 114 may be formed from any material that provides a fluid seal. The flexible film drape 114 may, for example, be an impermeable or semi-permeable, elastomeric material. Elastomeric material generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif. Other devices may be used in lieu of the flexible film drape 114 to form a fluid seal over the tissue site 102.

The attachment device 122 may be used to attach or help attach the flexible film drape 114 to the epidermis 107 or another layer, such as a gasket or additional sealing member. The attachment device 122 may take numerous forms. For example, the attachment device 122 may be a medically-acceptable, pressure-sensitive adhesive that is applied to the extension 124 of the flexible film drape 114. Alternatively, the pressure-sensitive adhesive may span the entire width of the flexible film drape 114. Alternative attachment devices 122 may include, but are not limited to, heat-activated adhesives, sealing tapes, double-sided sealing tapes, pastes, hydrocolloids, hydrogels, hooks, sutures, or other devices. In addition, the composition 103 also forms a fluid seal proximate the tissue site 102 and between the epidermis 107 and at least a portion of the flexible film drape 114. The composition 103 may augment or increase the strength of the seal provided by the attachment device 122 alone.

The composition 103 may address leaks or hair management in the periwound area. In some embodiments, the composition 103 may address both leaks and hair management in the periwound area. The composition 103 may be disposed at least proximate the peripheral edge 113 of the treatment manifold 112 and adjacent at least a portion of the epidermis 107. For example, the composition 103 may be disposed to touch the peripheral edge 113, or within a few centimeters of the peripheral edge 113. The composition 103 has a unified member or a portion that is soft in that it can flow over or otherwise move into crevices and imperfections in the epidermis 107 or flow around hair protruding from the epidermis 107 to make a substantial fluid seal. The composition 103 thereby forms a substantial fluid seal against the epidermis 107.

In addition, the composition 103 may be configured to modify the hair 105 on the epidermis 107 as the hair 105 encounters the composition 103. In this regard, the composition 103 may include a hair-modification agent to at least weaken the hair 105, i.e., inhibiting hair growth or dissolving the hair 105. Thus, the hair-modification agent may be a hair removal agent or a hair-growth inhibiting agent. The hair removal agent may be any active agent that removes hair. Some hair removal agents may require a barrier layer to protect the skin from irritation.

The hair removal agent may be a depilatory composition or the like. In some embodiments, the hair removal agent may be chemical depilatory compositions that typically cleave disulfide bonds in hair keratin, causing the hair fiber to disintegrate. Non-limiting examples of a hair removal agent include one or more of the following active agents: sulfhydryl compounds, thioglycolic acid and thioglycolate salts (for example calcium thioglycolate). Compounds which help to maintain a high pH (such as calcium hydroxide) will assist in the breakdown of the hair and can form advantageous complexes with thioglycolic acid sulfhydryl compounds. Sulfhydryl compounds include compounds having an —S—H group selected from the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically- or pharmaceutically-acceptable salts of any of the foregoing compounds. Mixtures of sulfhydryl compounds are suitable for use herein. Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof. More preferred sulfhydryl compounds include thioglycolic acid, cysteine, glutathione and N-acetyl-L-cysteine and cosmetically- and/or pharmaceutically-acceptable salts thereof. The most preferred sulfhydryl compound is N-acetyl-L-cysteine and cosmetically- or pharmaceutically-acceptable salts thereof.

Non-limiting examples of a hair-growth inhibiting agent include one or more of the following: 5-alpha reductase, ornithine decarboxylase, S-adenosylmethionine decarboxylase, gamma-glutamyl transpeptidase, transglutaminase, or wortmannin. Wortmannin (11-(acetyloxy)-1,6b,7,8,9a,10, 11,11b-octahydro-1-(methoxymethyl)-9a,11b-di-methyl-[1S-(1.alpha.,6b.alpha.,9a.beta.,11.alpha.,11b.beta.)]-3H-furo[4,3,2-de]indeno[4,5-h]-2-benzopyran-3,6,9-trione) is a fungal metabolite capable of entering intact cells and can induce cell death by apoptosis.

The reduced-pressure subsystem 120 includes a reduced-pressure source 126, which can take many different forms. The reduced-pressure source 126 provides reduced pressure. The reduced-pressure source 126 may be any device for supplying a reduced pressure, such as a vacuum pump, wall suction, micro-pump, or other source. In one embodiment, the reduced-pressure source may be a micro-pump associated with the flexible film drape 114. While the amount and nature of reduced pressure applied to the tissue site 102 will typically vary according to the application, the reduced pressure will typically be between −5 mm Hg and −500 mm Hg and more typically between −75 mm Hg and −300 mm Hg, and more typically still between −75 and −175 mm Hg. For example, and not by way of limitation, the pressure may be −75, −80, −90, −100, −110, −120, −130, −140, −150, −160, −170, −175 mm Hg or another pressure.

Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a reduction in absolute pressure.

In the illustrative embodiment of FIG. 1, the reduced pressure developed by the reduced-pressure source 126 is delivered through the reduced-pressure conduit 128, through canister 130, to a reduced-pressure interface 132. In one illustrative embodiment, the reduced-pressure interface 132 is a TRAC® technology port available from Kinetic Concepts, Inc. of San Antonio, Tex. The reduced-pressure interface 132 allows the reduced pressure to be realized within a sealed space 134 below the flexible film drape 114 and realized within the treatment manifold 112. The reduced-pressure interface 132 may also be a tube placed directly through the flexible film drape into the treatment manifold.

In operation according to one illustrative embodiment, the treatment manifold 112 is disposed proximate the tissue site 102, e.g., the wound 106. The composition 103 is at least disposed proximate the peripheral edge 113 of the treatment manifold 112 (and may go over the treatment manifold 112 as well in some embodiments). If the composition 103 has a release liner on a patient-facing side (see 164 in FIG. 7), the release liner is first removed. The tissue site 102, the treatment manifold 112, and a portion of the epidermis 107 can be covered by the flexible film drape 114 to form the sealed space 134. The flexible film drape 114 and the epidermis 107 are fluidly sealed at least in part by the composition 103. The sealed space 134 contains the treatment manifold 112. If not already coupled, the reduced-pressure interface 132 may be fluidly coupled to the sealed space 134. The reduced-pressure interface 132 may be fluidly coupled to the reduced-pressure source 126. The reduced-pressure source may be activated, and reduced pressure can be delivered to the sealed space 134.

As treatment progresses, hair encountering the composition 103 is modified to grow slower, to dissolve, or to otherwise be weakened. The weakened hair means the hair is relatively weaker than un-treated hair and may not tent the flexible film drape 114 or puncture the flexible film drape 114. In addition, if not already dissolved, weakened hair may readily break when the dressing is removed thereby minimizing pain to the patient.

Referring now primarily to FIG. 2, a cross-section is shown that illustrates the hair 105 encountering the composition 103. The hair 105 is extending into the composition 103 in this illustration. The hair-modification agent in composition 103 may act on the hair 105 to at least weaken the hair 105 as previously described. In addition, this cross section shows the composition 103 has portions that flow into imperfections 136, e.g., a crevice, in the epidermis 107 to form a substantial fluid seal.

As previously mentioned, numerous embodiments and features of the composition 103 are possible, but the use may substantially be the same. Additional embodiments and features are now presented. Referring now primarily to FIG. 3, a portion of an illustrative embodiment of a system for treating a tissue site 102 of the patient 104, which has hair 105 proximate the tissue site 102, with reduced pressure is presented. The system 100 is analogous in most respects to the system 100 of FIG. 1, and accordingly, some parts are labeled but not further described here. In addition, components referenced but not explicitly shown are analogous to those previously presented.

The system 100 includes a composition 103 that, in this illustrative embodiment, may be formed as an annular gel member 138. The annular gel member 138 may be shaped as a partial wedge member, as shown, or another shape, e.g., a rectangular disc. A partial wedge member may have a triangular cross-sectional profile. In some embodiments, the annular gel member 138 may have a peripheral portion that has a thickness less than a thickness of interior portions. The annular gel member 138 may be a blend of sealing and hair removal agents or may be formed as separate layers.

Figure 4:
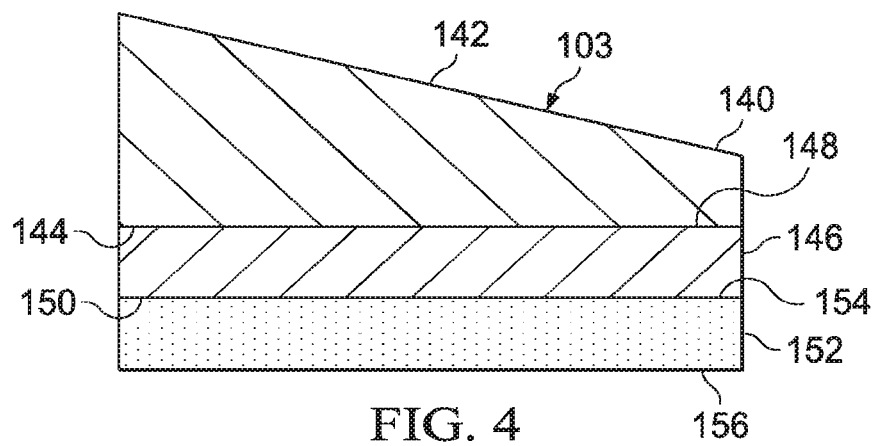
FIG. 4 is a cross sectional view of an illustrative embodiment of a composition for sealing and modifying hair.

Referring now primarily to FIG. 4, a cross-section of another illustrative embodiment of the composition 103 is presented. The composition 103 is analogous in most respects to the compositions 103 of FIGS. 1-3, and accordingly, some parts are labeled but not further described here. In addition, components referenced but not explicitly shown are analogous to those previously presented. In this example embodiment, the composition 103 is a hair-modification layer 140 disposed adjacent a barrier layer 146 and a sealing layer 152.

The hair-modification layer 140 of FIG. 4 has a first side 142 and a second side 144. The barrier layer 146 has a first side 148 and a second side 150, and the sealing layer 152 has a first side 154 and a second side 156. The barrier layer 146 substantially prevents or impedes the hair-modification layer 140 from migrating to the patient's epidermis. Thus, the barrier layer 146 may reduce the potential for skin irritation and allow for a more concentrated hair-modification agent to be used. In addition, the barrier layer 146 may minimize any unwanted interactions between the sealing layer, e.g., adhesive, and the hair-modification agent.

The second side 150 of the barrier layer 146 is disposed proximate the first side 154 of the sealing layer 152. The second side 144 of the hair-modification layer 140 is disposed proximate the first side 148 of the barrier layer 146.

The second side 156 of the sealing layer 152 may be covered with a release liner (not shown but analogous to release liner 164 in FIG. 7) prior to use.

The hair-modification layer 140 may be formed from a continuous phase member from a polymer matrix such as a soft acrylic, silicone, polyurethane, hydrogel or hydrocolloid into which a hair-modification agent has been dispersed or dissolved. The barrier layer 146 may be formed from polyolefin (gels, thermoplastic films, or elastomeric films), silicone, or polyurethane films. The sealing layer may be a soft acrylic, silicone, polyurethane, hydrogel, hydrocolloid, or polyolfin gels.

Figure 5:
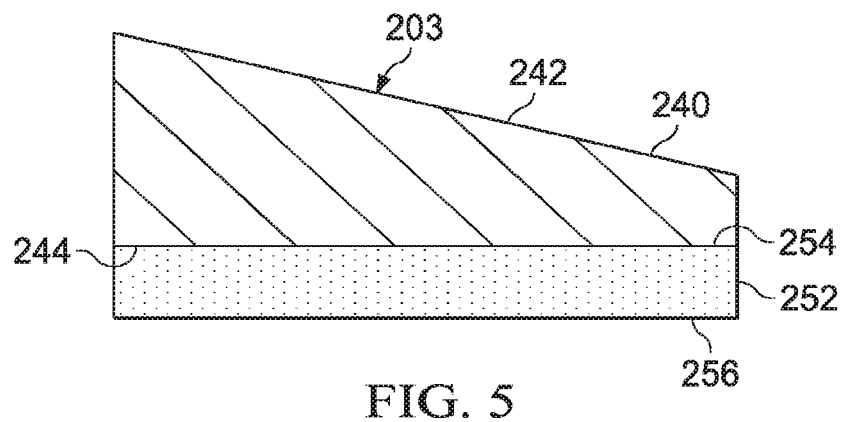
FIG. 5 is a cross sectional view of another illustrative embodiment of a composition for sealing and modifying hair.

FIG. 5 is a sectional view illustrating additional details of a composition 203. The composition 203 may be similar to the composition 103 described above with respect to FIGS. 1-4. Similar elements may have similar reference numbers that are indexed to 200. As shown in FIG. 5, the composition 203 may also be formed with only two layers: the hair-modification layer 240 adjacent the sealing layer 252. In this illustrative embodiment, the second side 244 of the hair-modification layer 240 is disposed proximate the first side 254 of the sealing layer 252.

Figure 6:
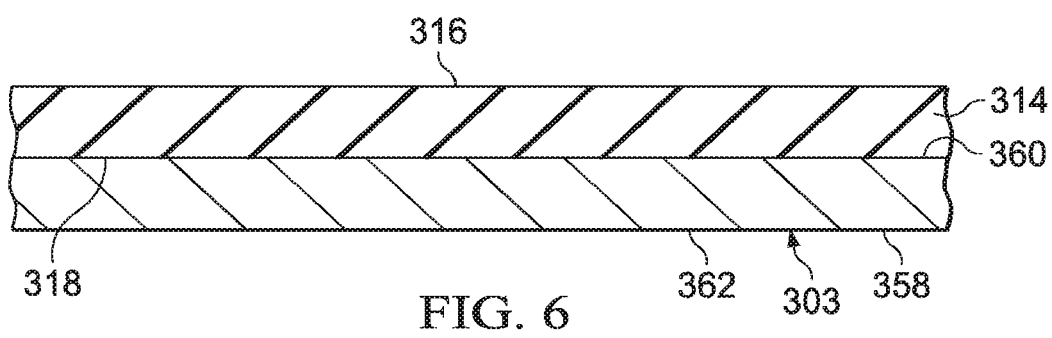
FIG. 6 is a cross sectional view of another illustrative embodiment of a composition for sealing and modifying hair disposed proximate a flexible film drape.

Referring now primarily to FIG. 6, another illustrative embodiment of a portion of a system for treating a tissue site, which has hair proximate the tissue site, with reduced pressure is presented. A composition 303 is shown that may be analogous in most respects to the composition 103 and the composition 203 of FIGS. 1-5, and accordingly, some parts are labeled but not further described here. Similar elements may have similar reference numbers that are indexed to 300. In this illustrative embodiment, a composition 303 and a flexible film drape 314 are combined. The flexible film drape 314 has a first side 316 and a second side 318. The composition 303 may include a layer 358 having sealing and hair modification properties, a first side 360, and a second side 362. The first side 360 of the layer 358 may be adjacent and coupled to the second side 318 of the flexible film drape 314. The layer 358 and the flexible film drape 314 are substantially co-extensive. In other words, the layer 358 substantially covers the second side 318 of the flexible film drape 314. The layer 358 includes a sealing agent or material and a hair-modification agent.

Figure 7:
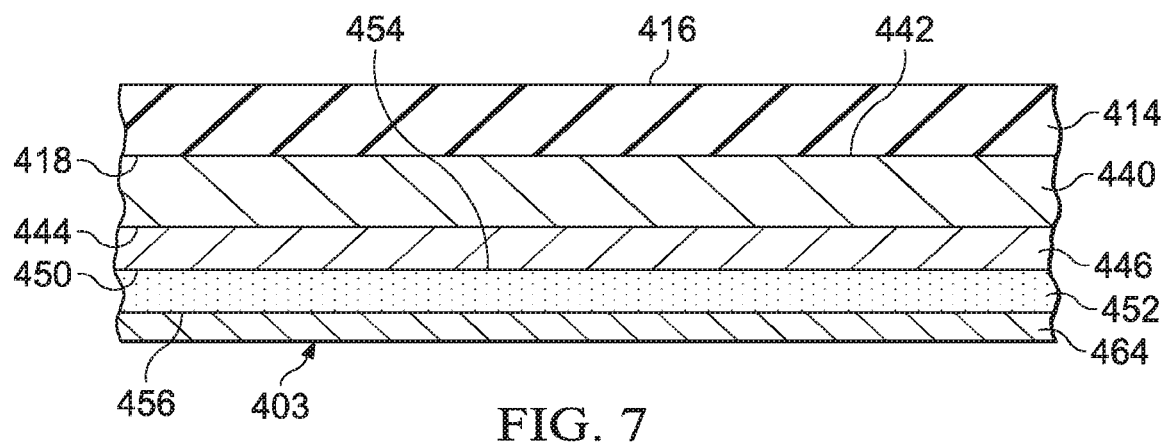
FIG. 7 is a cross sectional view of another illustrative embodiment of a composition for sealing and modifying hair disposed proximate a flexible film drape.

Referring now primarily to FIG. 7, another illustrative embodiment of a portion of a system for treating a tissue site, which has hair proximate the tissue site, with reduced pressure is presented. A composition 403 is shown that may be analogous in most respects to the composition 103, the composition 203, and the composition 303 of FIGS. 1-6, and accordingly, some parts are labeled but not further described here. Similar elements may have similar reference numbers that are indexed to 400. Like in FIG. 6, a composition 403 and a flexible film drape 414 are combined.

The composition 403 includes a hair-modification layer 440 having a first side 442 and a second side 444 and a barrier layer 446 having a first side 448 and a second side 450. The composition 403 may further include a sealing layer 452 having a first side 454 and a second side 456. The first side 448 of the barrier layer 446 may be proximate the second side 444 of the hair-modification layer 440. The first side 454 of the sealing layer 452 may be disposed proximate the second side of the hair-modification layer 440. The second side 456 of the sealing layer 452 may be covered by a release liner 464. The release liner 464 may be one or more of the following: a polyurethane film, high density polyethylene, polypropylene, a high-MVTR film, polymers such as acrylic copolymers, polyvinyl acetate, polyether block amide copolymers (PEBAX), polyvinyl alcohol and copolymers, polyamide, polyvinylchloride, casting paper, or polyvinylidene chloride.

The first side 442 of the hair-modification layer 440 is disposed proximate the second side 418 of the flexible film drape 414. The flexible film drape 414, the hair-modification layer 440, the barrier layer 446, and sealing layer 452 may be coupled, for instance, by mechanical interlocking, e.g., the barrier layer 446 may be a film and the layers 440, 452 may be soft and gel-like, and/or thermodynamic adhesion, e.g., the layers may be co-extruded or formed by multiple casting the hair-modification layer 440, the barrier layer 446, and the sealing layer 452 onto each other.

Figure 8:
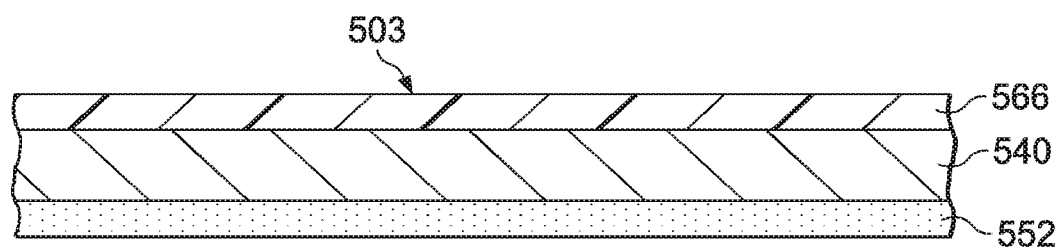
FIG. 8 is a cross sectional view of another illustrative embodiment of a composition for sealing and modifying hair.

Referring now primarily to FIG. 8, another illustrative embodiment of a composition 503 is presented. The composition 503 of FIG. 8 is analogous in most respects to the composition 203 of FIG. 5, except an odor layer 866 has been added. Similar elements may have similar reference numbers indexed to 800. The odor layer 866 may be a separate layer or may integrated into another layer or layers. The odor layer 866 may be formed from a material that inhibits or reduces odor. For example, the odor layer 866 may be formed from an activated carbon or clay.

Figure 9:
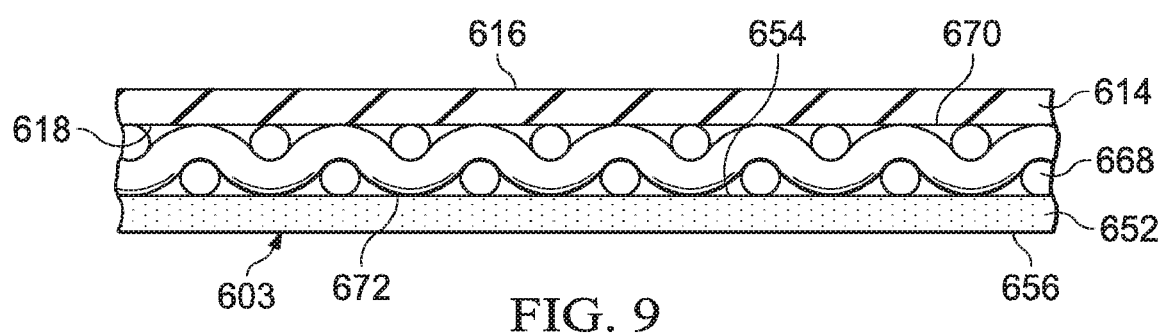
FIG. 9 is a cross sectional view of another illustrative embodiment of a composition for sealing and modifying hair disposed proximate a flexible film drape.

Referring now primarily to FIG. 9, another illustrative embodiment of a portion of a system for treating a tissue site, which has hair proximate the tissue site, with reduced pressure is presented. A composition 603 is illustrated. The composition 603 of FIG. 9 may be similar to and include elements similar to the composition 103, the composition 203, the composition 303, the composition 403, and the composition 503 of FIGS. 1-8. The similar elements may have similar numbers indexed to 600. The composition 603 may be formed with a fabric layer 668. The fabric layer 668 may be woven or non-woven and is impregnated with a hair-modification agent, i.e., a hair removal agent or hair-growth inhibiting agent. Impregnation of the fabric layer 668 may involve forcing a liquid substance into porous spaces of the fabric layer 668. Impregnation may combine the hair modification properties of the hair-modification agent with the properties of the fabric layer 668.

The fabric layer 668 has a first side 670 and second side 672. The composition 603 also includes a sealing layer 652 having a first side 654 and a second side 656. The first side 654 of the sealing layer 652 is disposed proximate the second side 672 of the fabric layer 668. The first side 670 of the fabric layer 668 is disposed proximate and coupled to the second side 618 of the flexible film drape 614. Alternatively, the fabric layer 668 may be laminated onto the flexible film drape 614. Alternatively, the flexible film drape 614 may be cast, for example, from melt, solution, or dispersion, onto the fabric layer 668. This illustrative embodiment may provide additional stiffness to the flexible film drape 614.

Figure 10:
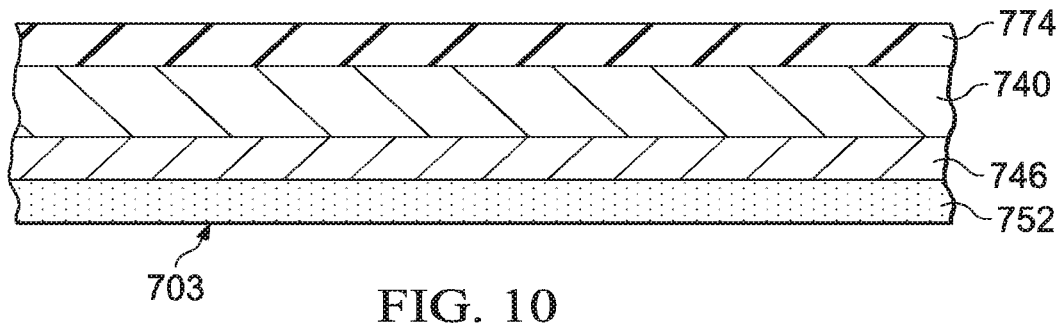
FIG. 10 is a cross sectional view of another illustrative embodiment of a composition for sealing and modifying hair.

Referring now primarily to FIG. 10, a cross section of another illustrative embodiment of a composition 703 is presented. The composition 703 is analogous in most respects to the composition 103, the composition 203, the composition 303, the composition 403, the composition 503, and the composition 603 of FIGS. 1-9, and accordingly, some parts are labeled but not further described here. Similar elements may be referenced by similar numbers indexed to 700. In addition, components referenced but not explicitly shown are analogous to those previously presented. The composition 703 differs from the embodiment of FIG. 4 in that an insulating layer 774 has been added. The insulating layer 774 may limit heat transfer from the patient through the areas that may be covered by the insulating layer 774. By limiting heat transfer, the insulating layer 774 may help inhibit hair growth. The insulating layer 774 may be foam or any material providing for the retention of heat. While the insulating later 774 is shown on the hair-modification layer 740, the insulating layer 774 may be located at other locations in the composition 703, e.g., the insulating layer 774 may be beneath (for orientation shown) the hair-removal layer 740 or beneath the barrier layer 746. The insulating layer 774 may be oriented beneath the hair-removal layer 740 and/or the barrier layer 746, in which case the insulating layer 774 may be formed of a soft gel thereby permitting hair to penetrate the insulating layer 774, which may be either a foam or contain bubbles or spheres, such as the filler sold under the trademark EXPANCEL, to increase heat insulation properties of the insulating layer 774. Alternatively, the insulating layer 774 may be oriented above the hair-removal layer 740 and/or the barrier layer 746, in which case the insulating layer 774 may be formed from a film, foamed or containing bubbles or spheres, or filled with insulating fillers, such as talc or silica.

Figure 11:
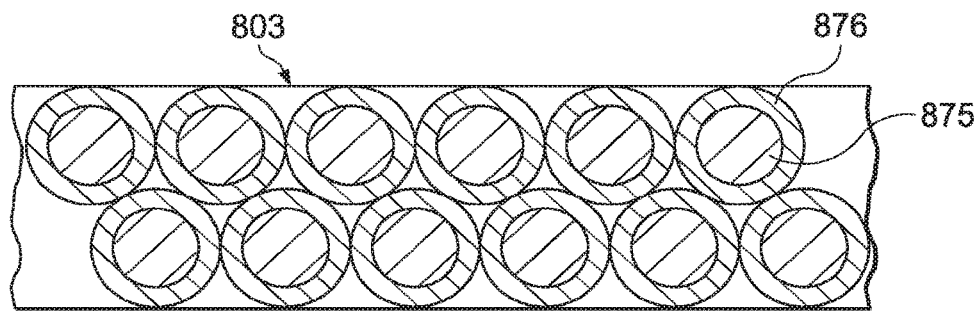
FIG. 11 is a cross sectional view of another illustrative embodiment of a composition for sealing and modifying hair.
Figure 12A:
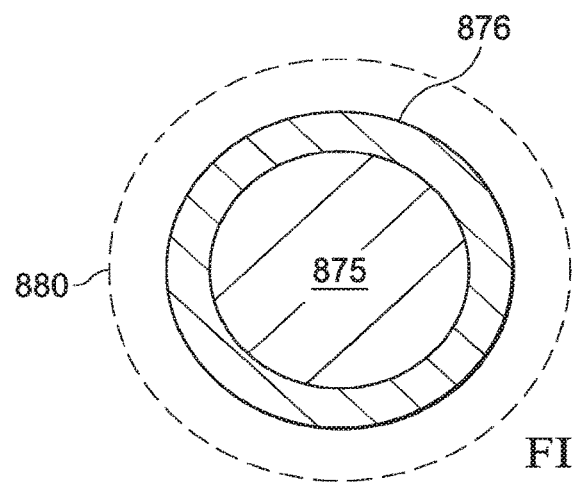
FIG. 12A is a cross sectional view of a portion of the composition for sealing and modifying hair of FIG. 11 showing an illustrative embodiment of a hair-modification agent encapsulated within an activateable shell that is shown in the un-activated state.
Figure 12B:
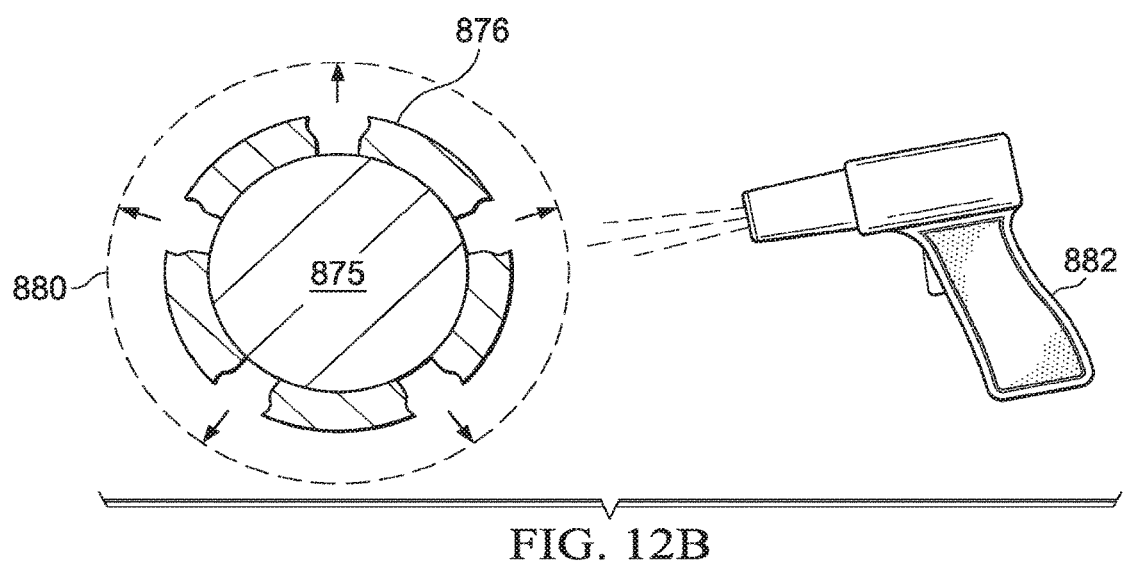
FIG. 12B is a cross sectional view of the portion of the composition for sealing and modifying hair of FIG. 12A showing the activateable shell in the activated state.

Referring now primarily to FIGS. 11-12B, another illustrative embodiment of a portion of a system for treating a tissue site, which has hair proximate the tissue site, with reduced pressure is presented. The system includes a composition 803 that includes hair-modification agent 875 encapsulated within an activateable shell 876. The composition 803 is analogous in most respects to the composition 103, the composition 203, the composition 303, the composition 403, the composition 503, the composition 603, and the composition 703 of FIGS. 1-10, and accordingly, some parts are labeled but not further described here. Similar elements may be referenced by similar numbers indexed to 800. In addition, components referenced but not explicitly shown are analogous to those previously presented. The activateable shell 876 has an un-activated state shown in FIG. 12A and an activated state shown in FIG. 12B. The hair-modification agent 875 may be any of the types referenced elsewhere herein. The hair-modification agent 875 may be within a single activateable shell 876 or more typically a plurality of activateable shells 876 or as shown in FIG. 11.

The activateable shell 876 may be configured to isolate the hair-modification agent 875 from the surroundings 880 when in the un-activated state (FIG. 12A). When the activateable shell 876 is in the activated state (FIG. 12B), the hair-modification agent 875 is not isolated from the surrounding 880, i.e., the hair-modification agent 875 may be in fluid communication with the surroundings 880. As shown in FIG. 12B, an activation device 882 may be used to activate the activateable shell 876 to change the activateable shell 876 from the un-activated state to the activated state.

In one illustrative embodiment, the activateable shell 876 may be formed from a phototriggerable microcapsule made of a polyamide. In this embodiment, the hair-modification agent 875 includes carbon nano tubes (CNT). The hair-modification agent is co-encapsulated with carbon nanotubes using interfacial polymerization. The incorporation of carbon nanotubes endows the activateable shells with the ability to response to an external optical event. The triggered or activated release of liquid from the activateable shell may be achieved with irradiation with a near-IR laser. Thus, the activation device 882 is a light gun that heats the CNT causing expansion that ruptures the activateable shell, thereby exposing the hair-modification agent 875. Other activateable shell types may be used with a corresponding variety of activation devices (e.g., heat, light, etc.). It should be apparent, that the embodiment of FIGS. 11-12B allows a user to choose when to activate the hair-modification agent 875.

It should be clear that the systems, devices, and methods described herein may be used with humans or with other animals. In this regard, it should be noted that the chemical composition of human hair and animal fur is the same (Keratin).

It should also be apparent that the systems, methods, and devices herein may provide numerous benefits. For example, hair growth can be managed through the treatment. Leaks—even low flow leaks—may be minimized or eliminated. A thin flexible film drape, e.g., 15 µm-60 µm, may be used which should relatively enhance the moisture-vapor-transmission rate. A thinner drape should allow for more comfort. Removal of the system or components described herein should be relatively less painful because of the absence of hair or at least weakened hair under the dressing.

The hair-modification agent and sealing agent may be associated in any of the ways shown above. The hair-modification agent and sealing agent may be in layers near each other or may be mixed or some combination.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, the release liner shown in FIG. 7, may be applied to any of the embodiments shown. As another example, the odor layer 566 of FIG. 8 may be added to any of the embodiments.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:
1. A system for treating a tissue site, the system comprising:
    a pad having a peripheral edge;
    a hair-modification agent adapted to be disposed adjacent the peripheral edge of the pad and further adapted to modify hair on an epidermis adjacent the tissue site;
    a barrier layer disposed adjacent to a side of the hair-modification agent; and a drape adapted to cover the pad, the hair-modification agent, and the barrier layer to form a sealed space containing the pad, the hair-modification agent, and the barrier layer.

2. The system of claim 1, wherein the hair-modification agent is dispersed in a continuous phase member with an adhesive.

3. The system of claim 1, wherein the hair-modification agent is selected from the group consisting of: thioglycolic acid, thioglycolate salts, calcium hydroxide, and sulfhydryl compounds.

4. The system of claim 1, wherein the hair-modification agent comprises a hair removal agent.

5. The system of claim 1, wherein the hair-modification agent comprises a hair-growth inhibiting agent.

6. The system of claim 5, wherein the hair-growth inhibiting agent comprises wortmannin.

7. The system of claim 1, wherein the hair-modification agent is dispersed in a gel member.

8. The system of claim 1, wherein the drape has a first side and a second side, and wherein the hair-modification agent covers the second side of the drape.

9. The system of claim 1, further comprising a release liner disposed adjacent a side of the barrier layer opposite the hair-modification agent.

10. The system of claim 1, further comprising an insulating layer.

11. The system of claim 1, wherein the hair-modification agent is disposed in a hair-modification layer.

12. The system of claim 1, wherein the hair-modification agent is dispersed in a polymer matrix.

13. The system of claim 12, wherein the polymer matrix comprises at least one of: an acrylic, a silicone, a polyurethane, a hydrogel, and a hydrocolloid.

14. The system of claim 1, wherein the hair-modification agent is dissolved within a polymer matrix.

15. The system of claim 1, wherein the barrier layer is formed from a material selected from the group consisting of polyolefins, silicone, and polyurethane.

16. The system of claim 1, wherein:
the hair-modification agent is impregnated in a fabric layer; and
the drape is disposed adjacent a side of the fabric layer.

17. The system of claim 16, wherein the fabric layer is a non-woven material.

18. The system of claim 16, wherein the fabric layer is a woven material.

19. The system of claim 1, further comprising a fabric layer laminated into the drape, wherein the hair-modification agent is impregnated in the fabric layer.

20. The system of claim 1, further comprising:
a shell encapsulating the hair-modification agent, the shell having a un-activated state and an activated state, wherein the shell fluidly isolates the hair-modification agent in the un-activated state, and the shell permits fluid communication with the hair-modification agent in the activated state; and
an activating device that is configured to change the shell from the un-activated state to the activated state.

21. The system of claim 20, wherein the shell comprises a polyamide shell and the activating device comprises a device that emits light.

22. A dressing for treating a tissue site, the dressing comprising:
a gasket, the gasket comprising:
a barrier layer; and
a hair-modification layer comprising a hair-modification agent configured to modify hair on epidermis adjacent the tissue site, the hair-modification layer associated with the barrier layer.

23. The dressing of claim 22, wherein the hair-modification agent is dispersed in a continuous phase member.

24. The dressing of claim 22, wherein the hair-modification agent is disposed in a polymer matrix.

25. The dressing of claim 22, wherein the gasket comprises an annular gel member.

26. The dressing of claim 22, wherein the hair-modification agent comprises a hair removal agent.

27. The dressing of claim 26, wherein the hair removal agent comprises at least one of: thioglycolic acid, thioglycolate salts, calcium hydroxide, and sulfhydryl compounds.

28. The dressing of claim 22, wherein the hair-modification agent comprises a hair-growth inhibiting agent.

29. The dressing of claim 28, wherein the hair-growth inhibiting agent comprises wortmannin.

30. The dressing of claim 22, wherein the hair-modification agent is encapsulated within a shell having an un-activated state and an activated state, in the un-activated state the shell fluidly isolates the hair-modification agent and in the activated state the shell permits fluid communication with the hair-modification agent.

31. The dressing of claim 22, further comprising an insulating layer.

32. A dressing for treating a tissue site, the dressing comprising:
a treatment pad having a peripheral edge;
a hair-modification layer having a hair-modification agent disposed therein, the hair-modification layer adapted to be disposed at least adjacent the peripheral edge of the treatment pad;
a barrier layer between the hair-modification layer and an epidermis; and
a drape adapted to cover the treatment pad, the hair-modification layer, and the barrier layer to form a sealed space containing the treatment pad, the hair-modification layer, and the barrier layer.

33. The dressing of claim 32, wherein the hair-modification layer is coupled to the drape.

* * * * *